United States Patent [19]

Groenewoud et al.

[11] Patent Number: 5,635,209
[45] Date of Patent: Jun. 3, 1997

[54] STABILIZED COMPOSITION OF LEVOTHYROXINE SODIUM MEDICATION AND METHOD FOR ITS PRODUCTION

[75] Inventors: Pieter J. Groenewoud; Hai Wang, both of Charlotte, N.C.

[73] Assignee: Vintage Pharmaceuticals, Inc., Charlotte, N.C.

[21] Appl. No.: 551,181

[22] Filed: Oct. 31, 1995

[51] Int. Cl.⁶ .................................................. A61K 9/20
[52] U.S. Cl. ........................ 424/464; 424/465; 424/488; 424/494
[58] Field of Search .................................. 424/464, 465, 424/475; 514/34

[56] References Cited

U.S. PATENT DOCUMENTS

| | | | |
|---|---|---|---|
| 4,110,470 | 8/1978 | Kummer et al. | 424/309 |
| 4,585,652 | 4/1986 | Miller et al. | 424/83 |
| 4,818,531 | 4/1989 | Anderson et al. | 424/111 |
| 5,001,115 | 3/1991 | Sloan | 514/34 |

Primary Examiner—Thurman K. Page
Assistant Examiner—William E. Benston, Jr.
Attorney, Agent, or Firm—Frank M. Caprio

[57] ABSTRACT

The invention discloses a medication which requires the combination of levothyroxine sodium and potassium iodide, with the potassium iodide acting as a stabilizing excipient, the presence of which results in a more stable levothyroxine sodium medication and provides for longer shelf life of the medication. A method for manufacturing the disclosed medication is also provided.

11 Claims, No Drawings

STABILIZED COMPOSITION OF LEVOTHYROXINE SODIUM MEDICATION AND METHOD FOR ITS PRODUCTION

INTRODUCTION

Levothyroxine sodium is prescribed in thyroid replacement therapy. It is often prescribed in tablet form. Clinically, levothyroxine sodium serves as specific replacement therapy for reduced or absent thyroid function of any etiology, including human ailments such as myxedema, cretinism and obesity, in non-exclusive particular. The levothyroxine sodium is normally expressed chemically as $C_{15}H_{10}I_4NaO_4XH_2O$. Levothyroxine sodium is not a very stable compound. It is well known that the stability of the levothyroxine sodium hormone is quite poor, since it is hygroscopic and degrades rapidly under conditions of high humidity or in the presence of other moisture sources or light and under conditions of high temperature, especially in the presence of other pharmaceutical excipients such as carbohydrates, including lactose, sucrose, dextrose and starch, as well as certain dyes. Due to this inherent instability, tablet formulations of levothyroxine sodium tend to degrade rapidly, particularly under conditions of high humidity and temperature. Gupts, et al, have reported that some tablets decompose by approximately 1% per month, while others decompose by up to 40% in 30 days once the bottles containing the tablets are opened. It is not uncommon for levothyroxine sodium tablets to be dispensed in quantities for up to 100 days' supply at a time. "Effect of Excipients on the Stability of Levothyroxine Sodium Tablets," *Journal of Clinical Pharmacy and Therapeutics*, (1990) 15, 331-336. It is, therefore, desirable to manufacture levothyroxine sodium tablets which are more stable than those known in the prior art, so that the percentage of the active ingredient of levothyroxine sodium will not diminish over time as quickly as with the more unstable tablets.

Various dry dosage formulations containing levothyroxine sodium, as well as processes of manufacture, are known in the art. U.S. Pat. No. 2,889,363, issued Jun. 2, 1959, to Ginger, et al and U.S. Pat. No. 2,889,364, dated Jun. 2, 1959, also to Ginger, et al., detail processes for producing thyroxine sodium. These prior art formulations experience stability problems.

One disclosure of a claimed stable dosage of levothyroxine sodium is found in U.S. Pat. No. 5,225,204, issued Jul. 6, 1993, to Chen, et. al., which details the use of polyvinylpyrrolidone or Poloxamer as a stabilizing complexing agent. The present invention differs from Chen's in several respects, not the least of which is in the use of potassium iodide as the stabilizing excipient.

The present invention discloses the use of potassium iodide as an excipient used in the manufacture of levothyroxine sodium medication, resulting in a more stable end product. It is an object of the invention to obtain a levothyroxine sodium tablet which retains its potency longer and, therefore, has a greater shelf life. It is a further object of this invention to develop a process by which to manufacture the more stable levothyroxine sodium medication and tablets.

THE INVENTION

In a preferred embodiment of the invention, a levothyroxine sodium trituration of 1.05% is obtained, with the other 98.95% of the trituration being composed of microcrystalline cellulose, NF PH101. The preferred embodiment also includes combining granulated potassium iodide with microcrystalline cellulose to form a potassium iodide granulation, such that the potassium iodide portion ranges from 0.1% to 0.7% of the granulation with the rest of the granulation being microcrystalline cellulose.

The more stable levothyroxine medication of the present invention is manufactured by physically combining the levothyroxine trituration with the potassium iodide granulation, and also adding croscarmellose sodium, which acts as a disintegrant, and magnesium stearate, which acts as a lubricant. A colored dye may also be used. The resulting combination may then be formed into tablets. By varying the concentration of the potassium iodide with respect to the microcrystalline cellulose in the potassium iodide granulation, the percentage of the levothyroxine sodium in the end product active ingredient is thereby varied. This allows for increasing or decreasing the strength of the active ingredient in tablets formed.

It is therefore an object of this invention to provide a stabilized formulation of levothyroxin sodium which resists degredation by light, heat, humidity or association with commonly used excipients.

Another object of this invention is to provide a stabilized dosage formulation complex of levothyroxine sodium and potassium iodide.

A still further object of this invention is to provide a stabilized complex of levothyroxine sodium which is capable of being mixed with suitable excipients and compressed into tablets or placed in capsules as dosage structures characterized by uniform distribution of levothyroxine sodium in the tablet matrix or capsule.

Another object of this invention is to provide a process for producing a stabilized dosage formulation containing levothyroxine sodium using potassium iodide as a stabilizing excipient.

Yet another object of this invention is to provide a method for producing stabilized levothyroxine sodium dosage formulations which are suitable for mixing with various pharmaceutically acceptable excipients and compression into tablets or filling capsules.

DETAILED DESCRIPTION OF THE INVENTION

The present invention discloses a new composition for levothyroxine sodium medication which provides for greater shelf life of levothyroxine sodium tablets, because the composition is more stable and less susceptible to degradation over time. The present invention also discloses a method for manufacturing the more stable composition.

In one embodiment of the invention, the levothyroxine sodium medication is prepared by combining the following components to create the final product:

Levothyroxine Sodium Trituration
Potassium Iodide Granulation
FD&C Yellow #6 Lake 38% Dye
D&C Yellow #10 Lake 15% Dye
Croscarmellose Sodium, NF
Magnesium Stearate, NF Levothyroxine Sodium Trituration The levothyroxine sodium trituration is made up of 1.05% levothyroxine sodium and 98.95% microcrystalline cellulose. In one embodiment of the invention, the microcrystalline cellulose is NF PH101, while the levothyroxine sodium is USP.

Potassium Iodide Granulation

The potassium iodide granulation component of the present invention is composed of potassium iodide and microcrystalline cellulose. The percentage of potassium iodide varies from 0.1% to 0.7% while the percentage of microcrystalline cellulose varies from 99.9% to 99.3%, respectively. In one embodiment of the invention, potassium iodide is dissolved in deionized water to make a potassium iodide solution. Microcrystalline cellulose is placed in a blender and the potassium iodide solution is slowly added to the blender to create a wet potassium iodide granulation. The microcrystalline cellulose is used as a carrier. Alternative carrier materials, known in the prior art, may also be used. The wet granulation is transferred to a drying apparatus. The drying process is continued until the granulation is dried to ±1.0% units of initial moisture. The granulation is then screened to provide a potassium iodide granulation of uniform particle size.

One embodiment of the invention uses a potassium iodide granulation consisting of 0.1% potassium iodide and 99.9% microcrystalline cellulose. In that embodiment, to prepare the potassium iodide granulation for an ultimate batch size of 3 million tablets, with each tablet containing 0.10 mg of potassium iodide, the potassium iodide granulation is prepared by dissolving 300.000 grams of potassium iodide into 60.00 kg of deionized water and adding to that solution 299.700 kg of microcrystalline cellulose.

In another embodiment of the invention wherein the potassium iodide granulation component is comprised of 0.70 mg of potassium iodide per tablet, to prepare a batch size of 3 million tablets, the potassium iodide granulation is prepared by dissolving 2100.000 grams of potassium iodide into 60.00 kg of deionized water, and thereafter adding to that solution 297.90 kg of microcrystalline cellulose.

Stabilized Levothyroxine Sodium Medication

The stabilized levothyroxine sodium medication is manufactured by combining the levothyroxine sodium trituration with the potassium iodide granulation, and other components. In one embodiment of the invention, a batch size of 1 million tablets is prepared with each tablet size being 100 mg. The relative strength of the levothyroxine sodium active ingredient in each 100 mg tablet is varied by varying the percentage of potassium iodide in the potassium iodide granulation used in the process. The dosage of the levothyroxine sodium per tablet typically varies from 25 µg per tablet, to 300 µg per tablet, and includes various dosages in between.

As an example, to create a batch of 1 million tablets of tablet size 100 mg each, with dosage of 100 µg of levothyroxine sodium per tablet, the following components and amounts are added together in a blender:

10.000 kg of Levothyroxine Sodium Trituration 1.05%

1,000.000 gm of Croscarmellose Sodium MF 20.000 gm of FD&C Yellow #6 Lake 38% Dye 310.000 gm of D & C Yellow #10 Lake 15% Dye 52.86 kg of microcrystalline cellulose with the KI granulation of 0.1%

35.31 kg of microcrystalline cellulose with the KI granulation of 0.7%

Varying the amount of potassium iodide will cause a variation in the dosages of levothyroxine sodium per tablet. The amount of potassium iodide required for a stabilized tablet with a levothyroxine sodium dosage of 25 µg, is four times the amount of levothyroxine sodium used. To obtain a more stable dosage of 300 µg of levothyroxine sodium, the ratio of potassium iodide to levothyroxine sodium is 1.5 to 1.

The components mentioned above are blended to ensure maximum physical mixing. Then 500.000 gm of magnesium stearate, NF, are added to the blended mixture, and the resulting combination is again blended to ensure maximum physical mixing. The resulting levothyroxine sodium medication is then compressed into tablets using known, prior art procedures. In one embodiment of the invention, the tablets are yellow, biconvex, round, and debossed, and the tablets weigh 100 mg, ±3%.

Testing Conducted to Show Stabilized Nature of New Medication

The medication disclosed herein was subjected to testing to determine the increased level of stability obtained by the addition of potassium iodide in the manner disclosed. What was desired was to determine the increased stabilization of the levothyroxine sodium 100 µg tablets over time, when subjected to the influence of a variety of environmental factors such as temperature and humidity. The length of the studies and the storage conditions were sufficient to cover the environment during normal storage, shipment, and subsequent use of levothyroxine sodium tablets. A short-term three month accelerated testing was carried out at a temperature of 40° C. and 75% relative humidity (RH) conditions for that temperature. The data obtained from the accelerated testing was used to evaluate the stability of the products.

Two batches of levothyroxine sodium tablets were subjected to the environmental testing. The first batch consisted of 100 µg tablets obtained from a current commercially available source. The second batch subjected to the identical testing was of the composition of the stabilized levothyroxine sodium medication as disclosed herein. Both batches were tested for the potency of the levothyroxine sodium active ingredients over time. The potency was tested at the following points in time: before being subjected to the environmental testing, and then every month thereafter over the three-month testing period.

Table 1 discloses the results of the test and indicates that the disclosed formulation of levothyroxine sodium medication in the present invention retains greater potency over time than other known formulations, and is therefore more stabilized.

TABLE 1

| | Percent Potency of Levothyroxine Sodium | |
|---|---|---|
| Time | Commercial Formulation | New Stabilized Formulation |
| Initial | 100% | 98.2% |
| 1 month | 95.4% | 98.6% |
| 2 month | 92.8% | 96.1% |
| 3 month | 86.2% | 95.7% |

What is claimed is:

1. A method of making levothyroxine sodium medication by combining together:

a. levothyroxine sodium mixed with a carrier;

b. potassium iodide mixed with a carrier;

c. a disintegrant, and d. a lubricant.

2. The method of claim 1, wherein the carrier is microcrystalline cellulose.

3. The method of claim 1, further comprising the addition of a colored dye.

4. A method of making levothyroxine sodium medication by combining together:

a. a mixture of levothyroxine sodium mixed with microcrystalline cellulose, said mixture comprised of 1.05% levothyroxine sodium and 98.95% microcrystalline cellulose;

b. a second mixture of potassium iodide mixed with microcrystalline cellulose, said second mixture comprised of potassium iodide ranging from 0.1% to 0.7% and microcrystalline cellulose ranging from 99.9% to 99.3%;

c. croscarmellose sodium;

d. magnesium stearate, and e. colored dye.

5. A medication consisting of the combination of levothyroxine sodium with potassium iodide.

6. The medication of claim 5 wherein said medication is in tablet form.

7. The medication of claim 5 wherein the ratio of potassium iodide to levothyroxine sodium ranges from 4 to 1 to 1½ to 1.

8. The medication of claim 5 wherein said medication is in tablet form and further wherein the dosage of levothyroxine sodium ranges from approximately 25 µg to 300 µg.

9. A method for making the medication of claim 6 wherein both the levothyroxine sodium component and the potassium iodide component are mixed with a carrier, and wherein said medication further comprises a disintegrant and a lubricant.

10. A method for making the medication of claim 5 by combining together:

a. a mixture of levothyroxine sodium mixed with microcrystalline cellulose, said mixture comprised of 1.05% levothyroxine sodium and 98.95% of microcrystalline cellulose, and b. a second mixture of potassium iodide mixed with microcrystalline cellulose, said second mixture comprised of potassium iodide ranging from 0.1% to 0.7% and microcrystalline cellulose ranging from 99.9% to 99.3%.

11. The method of claim 10, further requiring the combination of a disintegrant and a lubricant.

* * * * *

UNITED STATES PATENT AND TRADEMARK OFFICE
CERTIFICATE OF CORRECTION

PATENT NO. : 5,635,209

DATED : June 3, 1997

INVENTOR(S) : Wang, et al

It is certified that error appears in the above-identified patent and that said Letters Patent is hereby corrected as shown below:

On the title page, under item [19], "Groenewould" should read --Wang--.

On the title page, item [75], should read --Hai Wang, Pieter J. Groenewoud, both of Charlotte, N.C.--.

Signed and Sealed this

Twenty-fifth Day of November, 1997

Attest:

BRUCE LEHMAN

Attesting Officer

Commissioner of Patents and Trademarks